United States Patent [19]

Hill et al.

[11] 4,027,011

[45] May 31, 1977

[54] REARING PIGS

[75] Inventors: Ian Roland Hill, Eversley; Raymond Kenworthy, Catworth; Philip Porter, Putnoe, all of England

[73] Assignee: N.V. Internationale Octrooi Maatschappij "Octropa", Rotterdam, Netherlands

[22] Filed: May 19, 1976

[21] Appl. No.: 687,785

Related U.S. Application Data

[63] Continuation of Ser. No. 604,743, Aug. 14, 1975, abandoned, which is a continuation of Ser. No. 445,381, Feb. 25, 1974, abandoned, which is a continuation of Ser. No. 144,686, May 18, 1971, abandoned.

[30] Foreign Application Priority Data

June 3, 1970 United Kingdom ............ 26746/70

[52] U.S. Cl. .................................... 424/92; 424/87
[51] Int. Cl.² .................. A61K 39/02; A61K 39/40
[58] Field of Search ............................... 424/87, 92

[56] References Cited
FOREIGN PATENTS OR APPLICATIONS 62,894  7/1968  Germany

OTHER PUBLICATIONS

Vet. Bull. 38, No. 3912, No. 3416, No. 2959 (1968), 39, No. 2775, No. 3195, No. 935–936 (1969), 40, No. 3762–3765 (1970), 41, No. 3197, No. 3205 (1971).
Sojka, July, 1971, Vet. Bull. 41(7), 509–522, "Enteric Diseases in New–Born Piglets, Calves, and Lambs Due to *Escherichia coli* Infection".
Kohler, Dec., 1968, Am. J. Vet. Res., 29(12), 2263–2274, "Enterotoxic Activity of Filtrates of *Eschorichia coli* in Young Pigs".
Kohler, Kohler et al., May, 1971, Am. J. Vet. Res., 32(5), 731–737, 738–748, "Enterotoxic Activity of Whole Cell Lysates of *Escherichia coli* in Young Pigs; Feeding Bacteria–Free Whole Cell Lysates of *Escherichia coli* to Gnotobiotic Pigs".

*Primary Examiner*—Shep K. Rose
*Attorney, Agent, or Firm*—Barry Kramer

[57] ABSTRACT

To improve the resistance of pigs to gastro-intestinal disorders, the endotoxins of one or more of the pathogenic *E. coli* serotypes C8, 045, 0138, 0139, 0141, 0147 and 0149 are introduced into the pig intestine. Administration, which may for example be in water or in a pig feed, stimulates the pig intestine to produce antibodies to the *E. coli* organisms.

16 Claims, No Drawings

REARING PIGS

This is a continuation, of application Ser. No. 604,743, filed Aug. 14, 1975, which, in turn, is a continuation of application Ser. No. 445,381, filed Feb. 25, 1974, which, in turn, is a continuation of application Ser. No. 144,686, filed May 18, 1971, all of which prior applications are now abandoned.

This invention relates to the rearing of pigs, and is specially concerned with providing a regime to reduce their susceptibility to disorders of the gastro-intestinal tract.

These disorders frequently arise from the presence in the intestine of one or more pathogenic strains of the bacterium Escherichia coli, in particular those strains having the serotypes:

| Weybridge Classification | International Serotype Classification | |
|---|---|---|
| G7 | 08: K87 (B) | K88a,b(L) |
| E65 | 045: K | |
| E57 | 0138: K81 (B) | |
| E4 | 0139: K82 (B) | |
| E68II | 0141: K85a,b ⟶ K85a,c(B) | |
| G1253 | 0147: K89 (B) | K88a,c(L) |
| 'Abbotstown' | 0149: K91 | K88a,c(L) |

When the environment or diet of the pig is altered, for example when it is re-housed or weaned, the change in circumstances leaves the pig's system in a condition favourable to the proliferation of the pathogenic E. coli strains; and the gastro-intestinal disorders that may then result reduce the animal's general health and rate of weight gain, and often cause death.

The present invention arises from our discovery that the pig intestine can be simulated to produce antibodies to the pathogenic E. coli strains already present there by introducing into the intestine (as distinct from introducing into the blood stream, as by injection) the endotoxins of one or more of the aforesaid E. coli serotypes substantially free from the living E. coli organisms.

In specifying as 'endotoxins' the material to be introduced into the pig intestine, we do not mean to exclude from that material the presence of exotoxins or the presence of the cellular material within which the endotoxins are enclosed in the living bacterium; we mean merely that the endotoxins are of primary importance in obtaining the desired immunological effect while the exotoxins and cell debris are not. However, it will on occasion be convenient to leave either exotoxins or cell debris or both associated with the endotoxins; first, to save the trouble of separating them; and secondly, to enable such antigenic capacity as they possess to be utilised.

As already indicated, introduction into the intestine ('administration') of the endotoxins of one only of the aforesaid E. coli serotypes has some beneficial effect, insofar as the capacity of that serotype to cause harm will then be reduced. However, it is preferable to administer the endotoxins of all the serotypes. The endotoxins to be administered can be obtained by culturing each serotype (a sample of each of which is obtainable from the Central Veterinary Laboratory, Ministry of Agriculture and Fisheries. New Haw, Weybridge, Surrey, UK), and when growth of the micro-organism — and hence production of endotoxins — has proceeded to a suitable extent, to kill the proliferating micro-organisms, and release the endotoxins. This can be done by boiling or autoclaving. The whole sterilised cultures, each of which contains exotoxins and cell debris as well as endotoxins, can then be combined and administered. Preferably, however, instead of sterilising the whole cultures, the bacteria are separated (conveniently by centrifuging) and treated in a small volume of an aqueous medium (for example, water or saline) to kill the bacteria and cause releasse of endotoxins.

The simplest and most economic way of killing the separated bacteria is by heating. If heating is sufficiently prolonged — for example, 1 hour at 100° C, 20 minutes at 125° C — much of the endotoxin is freed from association with the cell walls of the killed bacteria and released into the medium in which heating is carried out. The residual bound endotoxins can, we have found, be brought into solution by treatment with an enzyme such as trypsin, lysozyme, pepsin, lipase or mixtures thereof. The results of typical treatment procedures are summarised in Table 1, which shows the relative proportions (titre) of endotoxins released into water by a preliminary treatment to kill the bacteria followed by an enzyme treatment to release endotoxin left bound to the bacterial cell walls.

TABLE 1

| | | Total endotoxin released by killing treatment followed by treatment of killed bacteria with enzyme for 1 hour at 37° C | | | | | | |
|---|---|---|---|---|---|---|---|---|
| Killing treatment - exposure to | Endotoxin released | trypsin | lysozyme | pepsin | lipase | lipase + trypsin | lysozyme + trypsin | lysozyme + pepsin |
| — | *320 | 1280 | 640 | 2560 | 1280 | 1280 | 1280 | 5120 |
| 100° C for 20 min | 1280 | 2560 | 1280 | 5120 | 2560 | 2560 | 5120 | 5120 |
| 125° C for 20 min | 2560 | 2560 | 2560 | 5120 | — | — | 5120 | 5120 |
| Ultrasonic waves (9 mm probe; 2.5 amps) at 0° C for 30 min | 640 | 2560 | 640 | 1280 | 1280 | 1280 | 640 | 320 |
| pH 3.5 at 45° C for 60 min | 640 | 640 | 320 | 640 | 320 | 1280 | 2560 | 5120 |
| 5% aqueous butanol at 37° C for 2 hours | 640 | 2560 | 2560 | 1280 | — | 1280 | 2560 | 1280 |

*Release due to naturallysis of micro organism

In practice, administration of the endotoxins to the pig is of course by the mouth, whether simply by forced dosing with sterilised culture material, or via the drinking water, or as an ingredient of a pig feed, suitably one containing the protein, the carbohydrate source such as cereal, and the vitamins and mineral elements that are essential components of the diet of pigs.

We have found that pig feed ingredients such as herring meal, yeast, wheatmeal, crushed oats, ground barley and skim milk powder have a tendency to bind E.

coli endotoxins to themselves at pH 5.9 and above, as shown by Table 2 below:

TABLE 2

| Diet ingredient | Titre of bound endotoxin per unit weight of ingredient at pH | | | | |
|---|---|---|---|---|---|
| | 5.3 | 5.9 | 6.3 | 6.8 | 7.2 |
| Wheatmeal | 0 | 480 | 480 | 480 | 560 |
| Crushed oats | 0 | 0 | 0 | 320 | 560 |
| Ground barley | 0 | 0 | 320 | 320 | 480 |
| Herring meal | 0 | 480 | 480 | 480 | 560 |
| Yeast | 0 | 320 | 480 | 480 | 560 |
| Skim milk powder | 0 | 320 | 480 | 480 | 560 |

We have also found that proteolytic enzymes, such as trypsin, are able to release the endotoxin bound in this way. Thus, at pH 7.2, trypsin releases about half the above bound endotoxin content of yeast and skim milk powder.

Additionally, we have found that E. coli endotoxins become precipitated from aqueous systems at a pH below 5, as shown by Table 3 below:

TABLE 3

| pH | Titre of endotoxin present in standard solution after adjustment to indicated pH |
|---|---|
| 7.0 | 320 |
| 6.5 | 320 |
| 6.0 | 320 |
| 5.5 | 320 |
| 5.0 | 320 |
| 4.5 | 160 |
| 4.0 | 80 |
| 3.2 | 40 |
| 2.5 | 40 |

It is convenient to incorporate the endotoxins in a feed by first making a pre-mix of the endotoxins with one of the feed ingredients (suitably skimmed milk) and water, and the mixing the pre-mix with the remaining ingredients of the feed. If this procedure is followed, it is desirable, having regard to the results summarised in Tables 2 and 3, to adjust the pre-mix to a pH value in the range 5 to 6, to ensure that on ingestion at least part of the endotoxins content of the feed is made immediately available for stimulation of the pig's intestinal immune system.

The invention has particular application in improving the resistance to infection of pigs at the weaning stage, when they are specially subject to stress. By feeding the endotoxin material before the pig is weaned, beginning say at the age of 4 to 10 days and continuing until weaning, the pig intestine can be stimulated to produce the appropriate antibodies, so that by the time the pig is taken from the sow, there is a high enough antibody circulation in the intestine to cope with any E. coli proliferation or at least to reduce the severity of any disease state that does develop. The endotoxin material can for this purpose be incorporated in a so-called "creep feed", that is to say a feed specially formulated to meet the nutrient requirements of pigs at the pre-weaning stage. The feed is put to the pigs with precautions to prevent the sow from eating it up, generally by making the feed accessible only via a narrow entrance.

Minimal dose rates are in the range 1 to 5 units (for measurement of a unit, see the Examples later) of the endotoxins of each E. coli serotype per pig per day. However, we have observed that pigs dosed at 1000 times this level showed no ill effects. A very suitable level for inclusion in a pig feed is $10^4$ to $10^5$ units of the endotoxins of each serotype per kg of feed.

The invention is illustrated by the following Examples.

EXAMPLE 1

Preparation and isolation of endotoxins.

Endotoxins are prepared from each of the seven E. coli serotypes earlier referred to, following generally the method of Westphal, Luderitz and Bister (1952) *Z.Natur.Forsch.* 7, 148.

A freeze-dried culture of E. coli is reconstituted in peptone water and incubated at 37° C for 6 hours. After suitable growth the culture is checked for purity on a washed sheep blood agar plate and then used to inoculate slopes of Nutrient Agar (Oxoid) in Roux flasks. The culture is grown at 37° C overnight and the bacteria are harvested in sterile distilled water. The bacterial suspension obtained is dispensed aseptically into 30 ml Universal bottles and centrifuged at 4,000 rpm for 10 minutes. The supernatant liquid is removed, and the residual pellet of bacteria is resuspended in 4 ml of sterile distilled water and then freeze-dried.

In order to isolate endotoxins, 0.5 g of freeze-dried E. coli is suspended in 5 ml of 0.15M NaCl, and 10 ml of 90% aqueous phenol is added as lysing agent. The mixture is heated at 68° C for 30 minutes with continuous agitation, following which it is centrifuged at 4,000 rpm to compact the cell debris. The aqueous phase is removed and cooled to 4° C, and to it are slowly added 10 volumes of ice-cold ethanol. The precipitate thus formed is redissolved in water, and nucleic acids are precipitated from the solution by addition of 2 volumes of ethanol, and removed. From the residual solution, endotoxins are precipitated by addition of a further 8 volumes of ethanol. They are separated by centrifugation, washed with ice-cold ethanol and re-dissolved in 0.15M NaCl. (This solution of endotoxins is referred to as Reagent 1.)

EXAMPLE 2

Assay of endotoxins a. Preparation of antiserum

Specific hyperimmune sera ('antisera') are prepared in New Zealand White rabbits against washed heat-killed (100° C, 2½ hours) organisms of each of the E. coli serotypes.

Suspensions of the heat killed organisms are prepared to 0.15M NaCl (approx 3 to $10^9$ organisms/ml) and injected intravenously. The immunisation schedule begins with an injection volume of 0.1 ml and is continued on every fourth day with doubling volumes to 1.6 ml. The rabbits are bled 10 days following completion of the schedule, and the blood obtained is centrifuged. The upper layer of hyperimmune serum is collected. (This antiserum is referred to as Reagent 2.)

b. Measurement of antibody (anti-endotoxins) activity in antiserum

Sheep erythrocytes are sensitised by treating a 5% suspension of washed packed cells with an equal volume of the endotoxin solution Reagent 1 at 37° C for 30 minutes. The sensitised cells are separated by centrifugation, washed free from excess endotoxins, and re-suspended in 0.15M NaCl to form a 2.5% suspension of endotoxin - sensitised sheep erythrocytes. (This is referred to as Reagent 3.)

Reagent 2 (the antiserum) is serially diluted with 0.15M NaCl to obtain a series of solutions of equal volume (1 vol) of antibody concentration 1/5, 1/10, 1/20, 1/40 ... $1/(5 \times 2^{n-1})$ that of Reagent 2, and to each of these solutions is added 1/5 vol of Reagent 3. Haemagglutination occurs in the stronger antiserum solutions and not in the weaker ones, and the end-point of the titration (assessed at 4° C) is taken as that solution in which hamagglutination only just occurs. In a typical procedure, the end point might be at the twelfth solution i.e. at the solution having an antibody concentration $1/(5 \times 2^{11})$ that of Reagent 2. Reagent 2 would be said to have an antiserum titre of $5 \times 2^{11}(=10,240)$.

c. Measurement of endotoxins concentration in solution of unknown concentration

The solution (Y) to be assayed is serially diluted with 0.15M NaCl to obtain a series of solutions of equal volume (3 vols) of endotoxins concentration 1/3, 1/16, 1/12, 1/24 &c that of the solution Y. To each of these solutions is added 1 vol of Reagent 2 (antiserum) diluted so as to have a titre of 20 (see b. earlier), and then (after a few minutes) 1 vol of Reagent 3 (sensitised sheep erythrocytes) giving final endotoxin concentrations 1/5, 1/10, 1/20 ... $1/(5 \times 2^{n-1})$ that of solution Y. Haemagglutination is inhibited in the stronger endotoxin solutions but does occur in the weaker ones, and the end-point of the titration is taken as that solution in which haemagglutination is only just inhibited. In a typical procedure this might be at the sixth solution, of endotoxins concentration $1/(5 \times 2^5)$ that of solution Y. Solution Y would then be said to have a titre of $5 \times 2^5(=160)$, equivalent to 160 units of endotoxin per ml (see Example 3).

EXAMPLE 3

A. Preparation of Endotoxin Material

The following procedure was separately followed for each of the E. coli serotypes earlier referred to.
i. The bacterium was streaked out from a depository stock culture onto washed blood agar plates and incubated at 37° C. for 24 hours. The plates were then conventionally checked for purity of strain.
ii. Colonies of the bacterium were transferred from the plates to 50 ml of Oxoid Nutrient Broth No. 2 (Catalogue No. CM 67). The broth was held at 37° C. for 24 hours.
iii. The whole culture obtained in (ii) was used to inoculate 1½ litres of Oxoid Nutrient Broth No. 2, and the broth was incubated, with shaking, at 37° C. for 24 hours. Each final culture thus produced contained about $10^{10}$ viable bacteria/ml, and a sample of the culture, when steamed at 125° C for 2 hours and submitted to the assay procedure of Example 2, gave a titre of 2560, corresponding to 2560 units of endotoxin per ml of steamed culture. The cultures of all the serotypes were pooled and the pool was steamed for 2 hours in an autoclave (125° C) to kill the bacteria.

B. Preparation of Pig Feed

The whole sterilised broth obtained from A is adjusted to pH 5 and incorporated in the weight ratio 15:85 in a conventional pig-weaning feed of the composition:

| | % by weight |
|---|---|
| roller-dried skimmed milk | 20 |
| white-fish meal | 25 |
| rolled oat groats (oat flakes) | 36 |

-continued

| | % by weight |
|---|---|
| sugar (sucrose) | 10 |
| dried yeast (75% unextracted) | 5.5 |
| cod liver oil | 2 |
| sodium chloride | 0.5 |
| mineral supplement | 1.0 |

The resulting mash is dried at 65° C. to a moisture level of about 15%.

EXAMPLE 4

The final culture of each serotype obtained following the procedure of A in Example 3 is centrifuged to separate the bacteria, which are then resuspended in water and heated at 125° C for 30 minutes. The killed bacteria are then treated for 3 hours at 37° C with a mixture of the enzymes lysozyme and pepsin, and the total endotoxins material resulting from the killing treatment and the enzymes treatment is assayed. The assayed endotoxins materials from all the serotypes are pooled, adjusted to pH 5, and added to skimmed milk. The mixture is then incorporated in a conventional pig feed of composition tabulated in Example 3, so as to give a concentration of $10^4$ units of the endotoxins of each serotype per kg of feed.

What is claimed is:

1. A method of improving resistance to infection by stimulating intestinal production of appropriate antibodies and thereby immunizing a pig against gastrointestinal disorders caused by certain selected pig pathogenic E. coli serotypes consequent on a change of environment or diet, comprising causing the pig to eat or drink an orally non-toxic composition comprising the water-soluble endotoxins freed from association with the bacterial cell walls of one or more of the pathogenic strains of E. coli bacterium having the serotypes 08, 045, 0138, 0139, 0141, 0147 and 0149, said endotoxins being stable to heating at 100° C. and said composition being substantially free from the living pathogenic E. coli organisms and being administered to the pig in amounts sufficient to stimulate the intestine of said pig to produce antibodies to said pathogenic E. coli organisms and with a frequency to maintain a daily circulation of said antibodies in the intestine.

2. A method as defined in claim 1 in which said endotoxins are administered in water.

3. A method as defined in claim 1 in which said endotoxins are administered in a pig feed.

4. A method as defined in claim 1 wherein said orally non-toxic composition comprises said water-soluble endotoxins of each of said E. coli serotypes.

5. A method as defined in claim 1 wherein said endotoxins are freed from association with the bacterial cell walls by heat sterilization of the whole live E. coli bacterial culture.

6. A method as defined in claim 5 wherein said heat sterilization is followed by enzymatic treatment with trypsin, lysozyme, pepsin, lipase or mixtures thereof to substantially release residual endotoxin left bound to the bacterial cell wall.

7. A method of improving resistance to infection by stimulating intestinal production of appropriate antibodies, and thereby immunizing a pig against gastrointestinal disorders caused by certain selected pig pathogenic E. coli serotypes upon weaning, comprising causing the pigs to eat or drink an orally non-toxic composition comprising the water-soluble endotoxins freed from association with the bacterial cell walls of one or more of the pathogenic strains of E. coli bacterium having the serotypes 08, 045, 0138, 0139, 0141, 0147 and 0149, said endotoxins being stable to heating at 100° C. and said composition being substantially free from the living pathogenic E. coli organisms and being administered to the pig beginning at the age of 4 to 10 days and continuing until weaning in amounts sufficient to stimulate the intestine of said pig to produce antibodies to said pathogenic E. coli organisms and thereby improve the resistance to infection of pigs at the weaning stage, when they are subject to stress and with a frequency such that by the time the pig is taken from the sow, there is an antibody circulation in the intestine sufficient to at least reduce the severity of any E. coli proliferation that develops.

8. A method as defined in claim 7 in which said endotoxins are administered in water.

9. A method as defined in claim 7 in which said endotoxins are administered in a pig feed.

10. A method as defined in claim 7 wherein said orally non-toxic composition comprises said water soluble endotoxins of each of said E. coli serotypes.

11. A pig feed comprising protein, a carbohydrate source, vitamins, mineral elements and water soluble endotoxins freed from association with the bacterial cell walls of one or more of the pathogenic strains of E. coli bacterium having the serotypes 08, 045, 0138, 0139, 0141, 0147 and 0149, said endotoxins being stable to heating at 100° C. and said pig feed being substantially free from living pathogenic E. coli organisms and containing said endotoxins in an amount that will provide effective improved resistance against infection by any of said selected pig pathogenic serotypes ranging from about 1 to 5 units of said endotoxins of each selected serotype per pig per day.

12. A pig feed as defined in claim 11 containing the water soluble entoxins freed from association with the baceterial cell wall of each of said E. coli 13. A pig feed as defined in claim 11 wherein said endotoxins are freed from association with the bacterial cell walls by heat sterilization of the whole live e. coli bacterial culture.

14. A pig feed as defined in claim 13 wherein said heat sterilization is followed by enzymatic treatment with trypsin, lysozyme, pepsin, lipase or mixtures thereof to substantially release residual endotoxin left bound to the bacterial cell wall.

15. A pig feed as defined in claim 11 in which said freed endotoxins are made into an aqueous premix with one or more ingredients of the feed at pH 5 to 6, and the premix is admixed with the remaining ingredients of the feed.

16. A pig feed as defined in claim 11 containing from $10^4$ to $10^5$ units of said freed endotoxins of each selected serotype per kilogram of feed.

* * * * *

UNITED STATES PATENT OFFICE
CERTIFICATE OF CORRECTION

Patent No. 4,027,011          Dated May 31, 1977

Inventor(s) Ian Roland Hill et al.

It is certified that error appears in the above-identified patent and that said Letters Patent are hereby corrected as shown below:

IN THE TITLE:

"Rearing Pigs" should read -- Oral Immunization Method For Pigs And Feed Composition Therefor --

In column 8, Claim 12, line 11, "wall" should read --walls--

In column 8, Claim 13, line 14, "live e." should read --live E.-

Signed and Sealed this

Twenty-seventh Day of September 1977

[SEAL]

Attest:

RUTH C. MASON
*Attesting Officer*

LUTRELLE F. PARKER
*Acting Commissioner of Patents and Trademark*